US012642889B2

(12) United States Patent
Ameer et al.

(10) Patent No.: US 12,642,889 B2
(45) Date of Patent: Jun. 2, 2026

(54) BIODEGRADABLE SOFT ELASTOMERS FOR REGENERATIVE ENGINEERING

(71) Applicants:Northwestern University, Evanston, IL (US); Ann and Robert H. Lurie Children's Hospital of Chicago, Chicago, IL (US)

(72) Inventors: Guillermo A. Ameer, Chicago, IL (US); Arun K. Sharma, Elmhurst, IL (US); Xinlong Wang, Evanston, IL (US); Matthew I. Bury, Lake Villa, IL (US)

(73) Assignees: Northwestern University, Evanston, IL (US); Ann and Robert H. Lurie Children's Hospital of Chicago, Chicago, IL (US)

( * ) Notice: Subject to any disclaimer, the term of this patent is extended or adjusted under 35 U.S.C. 154(b) by 1047 days.

(21) Appl. No.: 17/638,905

(22) PCT Filed: Aug. 31, 2020

(86) PCT No.: PCT/US2020/048678
§ 371 (c)(1),
(2) Date: Feb. 28, 2022

(87) PCT Pub. No.: WO2021/042015
PCT Pub. Date: Mar. 4, 2021

(65) Prior Publication Data
US 2022/0305176 A1 Sep. 29, 2022

Related U.S. Application Data

(60) Provisional application No. 62/894,450, filed on Aug. 30, 2019.

(51) Int. Cl.
| | |
|---|---|
| *A61L 27/52* | (2006.01) |
| *A61L 27/18* | (2006.01) |
| *A61L 27/38* | (2006.01) |

(52) U.S. Cl.
CPC ........... *A61L 27/3834* (2013.01); *A61L 27/18* (2013.01); *A61L 2430/22* (2013.01)

(58) Field of Classification Search
None
See application file for complete search history.

(56) References Cited

U.S. PATENT DOCUMENTS

| | | | |
|---|---|---|---|
| 8,445,016 B2 | 5/2013 | Santerre et al. |
| 2008/0206343 A1 | 8/2008 | Edinger et al. |
| 2010/0258977 A1 | 10/2010 | Sakurai et al. |
| 2010/0316614 A1 | 12/2010 | Sharma et al. |
| 2015/0231303 A1 | 8/2015 | Sharma et al. |
| 2015/0265749 A1 | 9/2015 | Sharma et al. |
| 2017/0202998 A1 | 7/2017 | Yang et al. |
| 2018/0154045 A1 | 6/2018 | Sharma et al. |
| 2018/0290965 A1 | 10/2018 | Brito et al. |
| 2022/0305176 A1 | 9/2022 | Ameer et al. |

FOREIGN PATENT DOCUMENTS

| | | | | |
|---|---|---|---|---|
| WO | WO-9835631 A1 * | 8/1998 | .......... | A61K 9/1641 |

OTHER PUBLICATIONS

Sharma et al. Urinary bladder smooth muscle regeneration utilizing bone marrow derived mesenchymal stem cell seeded elastomericpoly(1,8-octanediol-co-citrate) based thin films. Biomaterials. Aug. 2010;31(24):6207-17. Epub May 21, 2010. (Year: 2010).*
Xu et al. Polymer degradation and drug delivery in PLGA-based drug-polymer applications: A review of experiments and theories. J Biomed Mater Res Part B 2017:105B:1692-1716. (Year: 2017).*
International Search Report for PCT/US2020/048678. Mailed Dec. 8, 2020. 10 pages.
Dahms et al., Composition and biomechanical properties of the bladder acellular matrix graft: comparative analysis in rat, pig and human. Br J Urol. Sep. 1998;82(3):411-9.
Kohn et al., Effects of pH on human bone marrow stromal cells in vitro: implications for tissue engineering of bone. J Biomed Mater Res. May 2002;60(2):292-9.
Middleton et al., Synthetic biodegradable polymers as orthopedic devices. Biomaterials. Dec. 2000;21(23):2335-46.
Sharma et al., Cotransplantation with specific populations of spina bifida bone marrow stem/progenitor cells enhances urinary bladder regeneration. Proc Natl Acad Sci U S A. Mar. 5, 2013;110(10):4003-8.

* cited by examiner

*Primary Examiner* — Marcia S Noble
(74) *Attorney, Agent, or Firm* — Casimir Jones, S.C.; Rikki A. Hullinger

(57) ABSTRACT

Provided herein are materials and methods related to scaffolds and uses thereof. In some embodiments, provided herein are poly (octamethylene-octanol citrates) (POOC) scaffolds with native mechanical properties that are comparable to urinary bladder tissue. In some embodiments, provided herein are methods for the synthesis of POOC scaffolds with native mechanical properties that are comparable to urinary bladder tissue by including octanol in the polycondensation synthesis of POC. In some embodiments, provided herein are methods of use of the disclosed scaffolds, including for urinary bladder tissue regeneration.

11 Claims, 10 Drawing Sheets

FIG. 1A

POC          POOC

BIODEGRADABLE SOFT ELASTOMERS FOR REGENERATIVE ENGINEERING

RELATED APPLICATIONS

This application claims priority to U.S. Provisional Application No. 62/894,450, filed Aug. 30, 2019, the entire contents of which are incorporated herein by reference.

STATEMENT REGARDING FEDERALLY SPONSORED RESEARCH OR DEVELOPMENT

This invention was made with government support under DK109539 awarded by the National Institutes of Health. The government has certain rights in the invention.

FIELD

Provided herein are scaffolds and systems for cell/scaffold transplantation and uses thereof. In particular, provided herein are stem cell-seeded poly (octamethylene-octanol citrates) (POOC) scaffolds and methods of use, including for urinary bladder tissue regeneration.

BACKGROUND

Dysfunctional urinary bladders secondary to trauma or disease, including exposure to improvised explosive devices encountered by military personnel, spina bifida (SB), interstitial cystitis/painful bladder syndrome (IC/PBS), and cancer typically results in an end-stage urinary bladder and can require regenerative engineering procedures to reduce the risk of damage to the upper urinary tract including the kidneys. Although urinary bladder augmentation enterocystoplasty using an autologous bowel segment is the current gold standard reconstructive strategy, many side effects such as metabolic imbalances, perforation, infection, the potential for malignant cellular transformation, and stone formation are associated with this procedure. Alternatively, application of elastomeric scaffolds that mimic the mechanical properties of native urinary bladder tissue would be an ideal treatment for the end-stage dysfunctional urinary bladder. Small intestinal submucosa (SIS), a biological scaffolding material that is commercially available, has been used for urinary bladder regeneration studies. However, the batch-to-batch variance and inflammatory eliciting characteristics make it less than ideal for in vivo applications. Therefore, there is an urgent need to develop highly reproducible, non-toxic, biocompatible synthetic scaffolds with controllable mechanical properties to mimic the native urinary bladder environment.

BRIEF DESCRIPTION OF THE DRAWINGS

Figure 1A:
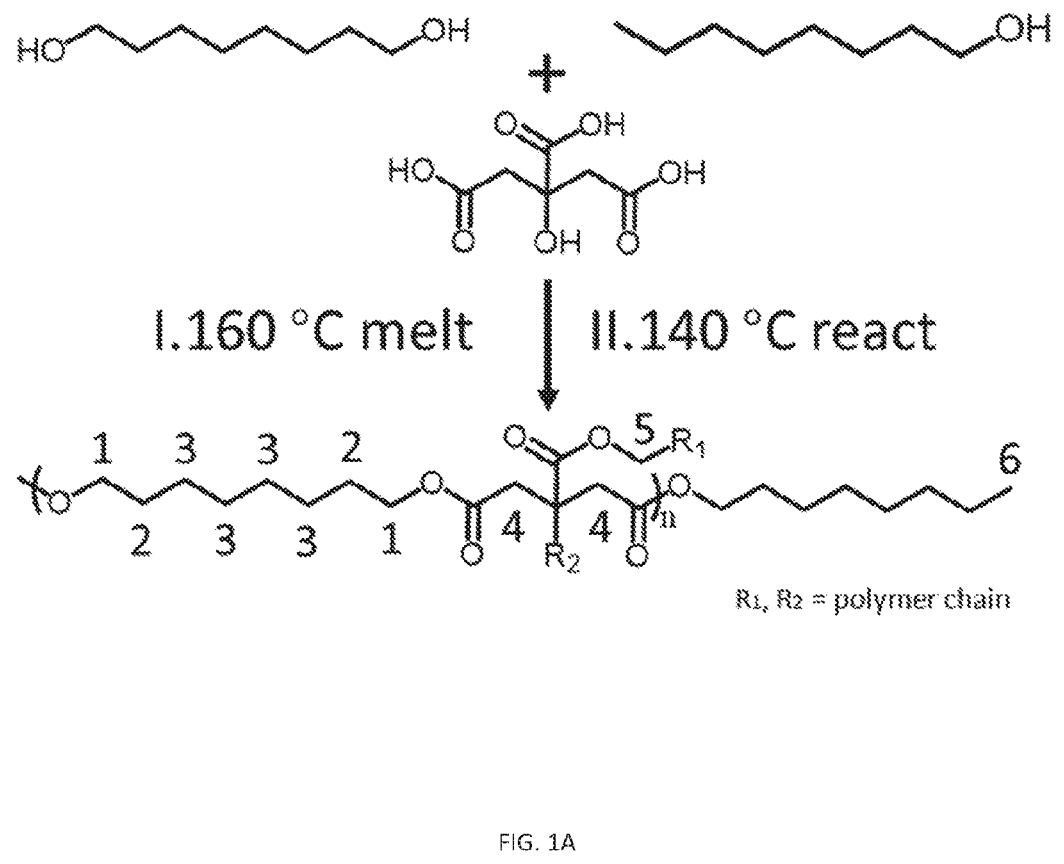

FIG. 1A shows a schematic representation of POOC pre-polymer synthesis process.

FIG. 2A) Deformation of POOC scaffold. FIG. 2B) Stress-strain curve of POOC scaffolds with various content of 1-octanol. FIG. 2C) Suture test of POC and POOC scaffold. Top: scaffold sutured onto mice abdominal wall; Bottom: scaffold after removing sutures. Arrows indicate the suture site.

SUMMARY

Figure 1B:
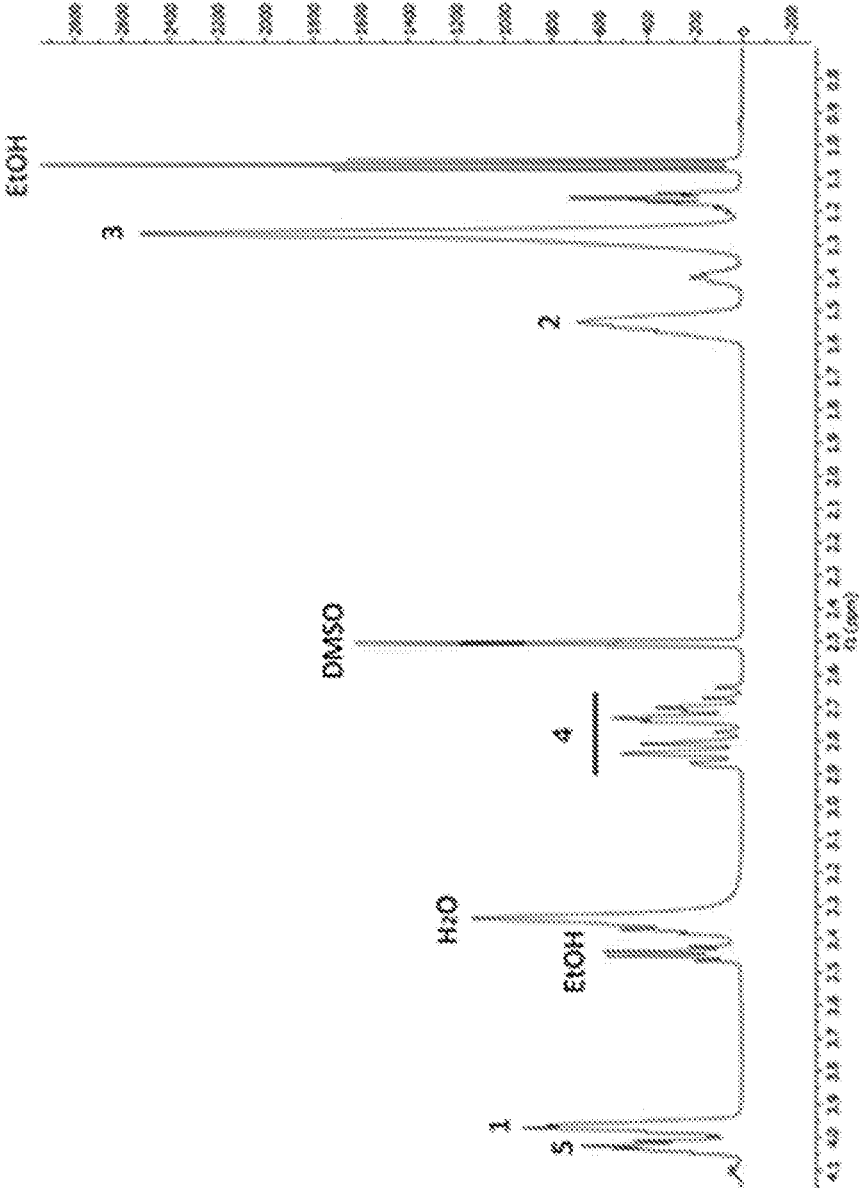
FIG. 1B-1C show the representative NMR spectrum of POC (B) and POOC pre-polymer (C).

Provided herein are materials and methods related to scaffolds and uses thereof. In some embodiments, provided herein are poly (octamethylene-octanol citrates) (POOC) scaffolds with native mechanical properties that are comparable to urinary bladder tissue. In some embodiments, provided herein are methods for the synthesis of POOC scaffolds with native mechanical properties that are comparable to urinary bladder tissue by including octanol in the polycondensation synthesis of POC. In some embodiments, provided herein are methods of use of the disclosed scaffolds, including for urinary bladder tissue regeneration.

Definitions

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise.

As used herein, the term "about," when referring to a value is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "bladder augmentation" refers to a surgery performed to increase the capacity of the urinary bladder. Urinary bladder augmentation may be performed using a scaffold, such as cell-seeded scaffold, described herein.

As used herein, "culturing" refers to propagating or nurturing a cell, collection of cells, tissue, or organ, by incubating for a period of time in an environment and under conditions which support cell viability or propagation. Culturing can include one or more of the steps of expanding and proliferating a cell, collection of cells, tissue, or organ according to the invention.

The term "isolated", as used herein in relation to a cell, as in "an isolated cell" or "isolated cells" refers to cells that are separated and enriched in a sample so as to remove the isolated cell(s) from other cells with which it is ordinarily associated in its natural environment. For example, isolated stem cells are stem cells that are removed from their natural environment and enriched in a sample, such that the sample housing the stem cells contains a higher percentage of stem cells than a corresponding sample found in a tissue in its natural environment.

As used herein, the term "progenitor cell" refers to a cell that has the capacity to both proliferate, giving rise to more progenitor cells, and differentiate into one or more specific cell types or to form a specific type of tissue. "Progenitor cells" generally exhibit oligopotency, in that they are capable of differentiating into a variety of cell types. This includes uncommitted cells, preferably of mammalian origin, that are competent to differentiate into one or more specific types of differentiated cells, depending on their genomic repertoire and the tissue specificity of the permissive environment in which morphogenesis is induced. Preferably, morphogenesis culminates in the formation of differentiated tissue having structural and function properties of a tissue that occurs naturally in the body of a mammal. A primary difference between a "progenitor cell" and a "stem cell" is that progenitor cells are more limited in the types of cells it can become, and cannot divide and reproduce indefinitely.

As used herein, a "recipient" refers to a mammal that receives an organ, tissue or cells taken from a donor. As used herein, a "donor" is a mammal from which organs, tissues or cells are taken for transplant into a recipient. In the case of autologous stem cells, the donor and recipient are the same subject.

As used herein, the term "stem cell" or "undifferentiated cell" refers to self-renewing multipotent cells that are capable of giving rise to more stem cells, as well as to various types of terminally differentiated cells. The term "hematopoietic" as used herein refers to a type of stem or progenitor cell that can develop into all types of blood cells, including white blood cells, red blood cells, and platelets. The term "hematopoietic stem and progenitor cells" or "HSPCs" as used herein is inclusive of both hematopoietic stem and hematopoietic progenitor cells.

As used herein, the term "subject" refers to any animal including, but not limited to, insects, humans, non-human primates, vertebrates, bovines, equines, felines, canines, pigs, rodents, and the like. The terms "subject" and "patient" may be used interchangeably. A subject may be of any stage of life (e.g. embryo, fetus, infant, neonatal, child, adult, etc.). A subject may be male or female.

As used herein, the terms "treat," "treatment," and "treating" refer to reducing the amount or severity of a particular condition, disease state (e.g., dysfunctional urinary bladder), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

DETAILED DESCRIPTION

In some aspects, provided herein are scaffolds for tissue engineering. In some embodiments, provided herein are scaffolds for use in urinary bladder tissue engineering.

The scaffold comprises poly (octamethylene-octanol citrate) (POOC). The scaffold provided herein is advantageous over other scaffolds currently used in the field, as it displays native mechanical properties that are comparable to urinary bladder tissue.

In some embodiments, the scaffold comprises a web, matrix, and/or thin film. In particular embodiments, the scaffold is configured to form a thin film. In some embodiments, a scaffold is a 3D scaffold. In some embodiments, a scaffold provides the support for cells to proliferate and maintain their capacity to differentiate. In some embodiments, a POOC scaffold as described herein provides a flexible, biodegradable, non-toxic, and/or sutural thin-film scaffold. In some embodiments, POOC exhibits the capacity to function as a useful scaffold in both in vivo and in vitro settings. In some embodiments, a POOC scaffold is transplantable with a desired cell mixture. In some embodiments, a scaffold (e.g. POOC scaffold) provides a substrate upon which to transplant a desired cells or mixture of cells. In some embodiments, a scaffold (e.g. POOC scaffold) provides a growth surface and/or material for a desired cell mixture upon transplantation. In some embodiments, a scaffold (e.g. POOC scaffold) is configured to remain as part of new tissue (e.g. urinary bladder tissue) following transplant. In some embodiments, a scaffold (e.g. POOC scaffold) is configured to remain associated with transplanted cells and/or regenerated tissue (e.g. urinary bladder tissue). In some embodiments, a scaffold (e.g. POOC scaffold) is configured to degrade following transplantation (e.g. hours after transplantation, days after transplantation, weeks after transplantation, months after transplantation, years after transplantation, etc.). In some embodiments, a scaffold (e.g. POOC scaffold) is configured to degrade following tissue regeneration (e.g. hours after transplantation, days after transplantation, weeks after transplantation, months after transplantation, years after transplantation, etc.).

The POOC scaffold may be created by reacting 1,8-octanediol, citric acid, and 1-octanol. In some embodiments, the POOC scaffold 1-29% 1-octanol. In some embodiments, the POOC scaffold comprises 5-25% 1-octanol. In some embodiments, the POOC scaffold comprises 10-20% 1-octanol. In some embodiments, the POOC scaffold comprises 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29% 1-octanol. In particular embodiments, the POOC scaffold comprises 20% 1-octanol.

In some aspects, provided herein are systems comprising a scaffold as described herein. In some embodiments, provided herein are cell transplantation systems. The cell transplantation system comprises a POOC scaffold as described herein, and a population of cells. Suitable populations of cells are described in U.S. Patent Publication No. 20150231303, U.S. Patent Publication No. 20100316614, U.S. Patent Publication No. 20150265749, and U.S. Patent Publication No. 20180154045, the entire contents of each of which are incorporated herein by reference.

In some embodiments, the population of cells are autologous (i.e., derived from the subject for which administration of the scaffold is intended). In some embodiments, at least a portion of the population of cells are derived from a different donor (i.e., not derived from the subject for which administration of the scaffold is intended).

In some embodiments, the population of cells comprises a population of mesenchymal stem cells (MSCs). In some embodiments, the population of cells comprises a population of hematopoietic stem/progenitor cells (HSPCs). In some embodiments, the population of cells comprises bone marrow derived HSPCs. In some embodiments, the population of cells comprises a mixture of MSCs and HSPCS.

In some embodiments, the population of cells may comprise desired markers, which may be used to select for a desired cell type. For example, it may be desirable for the population of cells to comprise a population of CD34$^+$ HSPCs. CD34$^+$ HSPCs have demonstrated the ability to induce angiogenesis and vasculogenesis, and therefore may provide a viable means for tissue revascularization in vivo. Furthermore, CD34$^+$ HSPCs co-transplanted with donor-matched MSCs have been shown to cause a dramatic increase in tissue vascularization as well as an induction of peripheral nerve growth in grafted areas compared with samples not seeded with HSPCs (Sharma et al., PNAS 110; 10: 4003-4008 (2013), incorporated herein by reference in its entirety).

In some embodiments, at least a portion of the population of HSPCs are CD34$^+$ HPSCs. For example, at least 50% (e.g. at least 50%, at least 60%, at least 70%, at least 80%, at least 90%, at least 95%, at least 99%) of the population of HSPCs may be CD34$^+$ HPSCs. In some embodiments, at least 50% of the population of HPSCs are CD34$^+$ HPSCs. In some embodiments, at least 90% of the population of HPSCs are CD34$^+$ HPSCs. In some embodiments, the MSCs are bone marrow MSCs (BM MSCs). Alternative sources of MSCs may also be used, including MSCs derived from adipose tissue, dental pulp, mobilized peripheral blood and birth-derived tissues (e.g. placenta, umbilical cord).

In some embodiments, the population of cells comprises a population of bone marrow MSCs and a population of CD34$^+$ HPSCs.

The population of cells may be isolated from any suitable source. In some embodiments "isolating" a cell or cell population refers to the process of removing cells from an organism or tissue sample and separating away other cells which are not the desired cell type. For example, an isolated BM MSC population will be generally free from contamination by other cell types and will generally have the capability of propagation and differentiation to produce mature cells of the tissue from which it was isolated. However, when dealing with a collection of stem cells, e.g., a culture of stem cells, it is understood that it is practically impossible to obtain a collection of stem cells which is 100% pure. Therefore, an isolated stem cell can exist in the presence of a small fraction of other cell types which do not interfere with the utilization of the stem cell for analysis or production of other, differentiated cell types. Isolated stem cells will generally be at least 30%, 40%, 50%, 60%, 70%, 80%, 85%, 90%, 95%, 98%, or 99% pure. Preferably, isolated stem cells according to the invention will be at least 98% or at least 99% pure.

In some embodiments, cells are isolated by any suitable techniques (e.g., flow cytometry, fluorescence-activated cell sorting (FACS), etc.). In some embodiments, fluorescence is utilized in cell sorting to isolate the desired cell populations. Any suitable means of detecting the fluorescently labeled cells can be used. The cells may be identified using epifluorescence optics, and can be physically picked up and brought together by Laser Tweezers (Cell Robotics Inc., Albuquerque, N. Mex.). They can be separated in bulk through FACS.

In some embodiments, the scaffold is seeded with the population of cells. Seeding may be performed by any suitable method, including the methods described herein. The proper number of cells to be added to the scaffold, selection of culture media, duration of cell seeding, etc. may be adjusted as necessary depending on the specific cell type used. In exemplary embodiments, MSCs (e.g., bone marrow MSCs) may be seeded onto the scaffold prior to administration to a subject. In some embodiments, multiple incubations of the scaffold with the MSCs may be performed in order to achieve the desired cell density on the scaffold. In some embodiments, after seeding with MSCs, seeding with HPSCs (e.g. CD34$^+$ HPSCs) may be performed.

The scaffold and/or cell transplantation systems described herein may find use in a method of regenerating tissue in a subject in need thereof. Although the methods provided herein are frequently discussed in relation to regeneration of urinary bladder tissue, the scaffolds and systems described herein may be provided to a subject to regenerate other soft tissues. Other soft tissues that may be regenerated using a scaffold as described herein include, for example, muscles, tendons, ligaments, fascia, nervous, fibrous tissues, blood vessels, and synovial membranes. For regeneration of such tissue, an appropriate cell population may be selected to be used in combination with a scaffold disclosed herein to promote tissue regeneration. Selection of the appropriate cell types may depend on the exact soft tissue to be regenerated.

In some embodiments, a cell transplantation system described herein (e.g. a system comprising a POOC scaffold and a defined population of cells) may be provided to a subject to regenerate tissue (e.g. urinary bladder tissue) in the subject. In some aspects, provided herein are methods for regenerating tissue in a subject. The method may comprise administering to the subject a scaffold or cell transplantation system as described herein. For example, the method may comprise administering to the subject a cell transplantation system comprising a poly (octamethylene-octanol citrate) (POOC) scaffold and a population of cells as described herein.

In some embodiments, methods described herein provide an alternative to urinary bladder augmentation enterocystoplasty. For example, the methods may provide an alternative to urinary bladder augmentation enterocystoplasty for patients who maintain a normal bone marrow microenvironment such as those suffering from urinary bladder trauma or localized urinary bladder cancer. In some embodiments, the cell transplantation systems described herein may be provided to a subject suffering from interstitial cystitis/ painful bladder syndrome (IC/PBS). IC/PBS is a state in which there is chronic pain and discomfort of the urinary bladder and surrounding pelvic region.

In some embodiments, diseased tissue (e.g. diseased urinary bladder tissue) is removed from the subject and replaced with a cell transplantation system as described herein. In some embodiments, the cell transplantation system is administered to the subject by surgical techniques, such as anastomosis. For example, administering the cell transplantation system to the subject may comprise anasto- mosing the cell-seeded scaffold to the urinary bladder of the subject.

The POOC scaffolds described herein, and cell transplan- tation systems comprising the same, are advantageous over other scaffolds previously used in the art. Biocompatible elastomeric scaffolds using poly (octamethylene citrate) (POC) have previously been developed. Despite successful regeneration of urinary bladder tissue in a rat model of urinary bladder augmentation, a relative higher Young's modulus (0.8 MPa) compared to that of human (0.25 MPa) limited clinical application potential. The elastic modulus of a human urinary bladder is within the hundreds of kPas, while typical scaffolds that are currently used for urinary bladder tissue engineering such as non-woven PLGA, PGA, and collagen can be found in the MPa to GPa range with relatively inefficient elongation characteristics (<10%) thus making them rigid and non-contractile (Dahms et al. Br J Urol 1998; 82(3):411-419; Middleton & Tipton. Biomateri- als 2000; 21(23):2335-2346; herein incorporated by refer- ence in their entireties). Furthermore, the degradation of these polymers typically results in a decreased localized pH, causing an adverse effect upon cells in the vicinity (Kohn et al. J Biomed Mater Res 2002; 60(2):292-299; herein incor- porated by reference in its entirety).

EXAMPLES

Example 1

Described herein is a poly (octamethylene-octanol cit- rates) (POOC) scaffold along with suitable methods for synthesizing the same.

Methods for fabrication of a biocompatible elastomeric POOC scaffold with native tissue mechanical properties which has great potential for application in urinary bladder augmentation enterocystoplasty are provided herein. In addition, the strategy can be applied more broadly to support regeneration of other soft tissues. The mechanical properties of materials used in urinary bladder augmentation entero- cystoplasty is critically important for urinary bladder tissue regeneration. However, most synthetic scaffolds have mis- matched mechanical properties as compared directly to native urinary bladder tissue which results in many side effects such as perforation, incontinence, and leakage.

The disclosed scaffolds have several advantages over existing technologies. For example, compared to autologous bowel segment, the POOC scaffold can be easily acquired without any damage to intestine. Compared to SIS, fabrica- tion of POOC scaffolds are more controllable which can reduce the batch-to-batch variance. The containing antioxi- dant citrates can also prevent in vivo inflammatory responses. Compared to conventional POC scaffolds, the POOC scaffolds are more elastic which can better mimic the mechanical properties of native urinary bladder tissue. In addition, they are more deformable and suturable, which is beneficial for use in surgical procedures. Compared to grafting of unseeded scaffolds, the POOC scaffold seeded with autologous bone marrow derived stem cells can facili- tate urinary bladder tissue regeneration processes.

In order to better mimic the mechanical properties of human urinary bladder tissue, octanol is used as a capping reagent when synthesizing the POOC polymer. Briefly, the synthesis procedures of transplantable POOC scaffold can be divided into three steps: 1) synthesis and purification of POOC pre-polymer; 2) casting and leaching of POOC scaffold; 3) mesenchymal stem cells (MSCs) and CD34$^+$ hematopoietic stem/progenitor cells (HSPCs) seeding pro- cess.

Figure 1C:
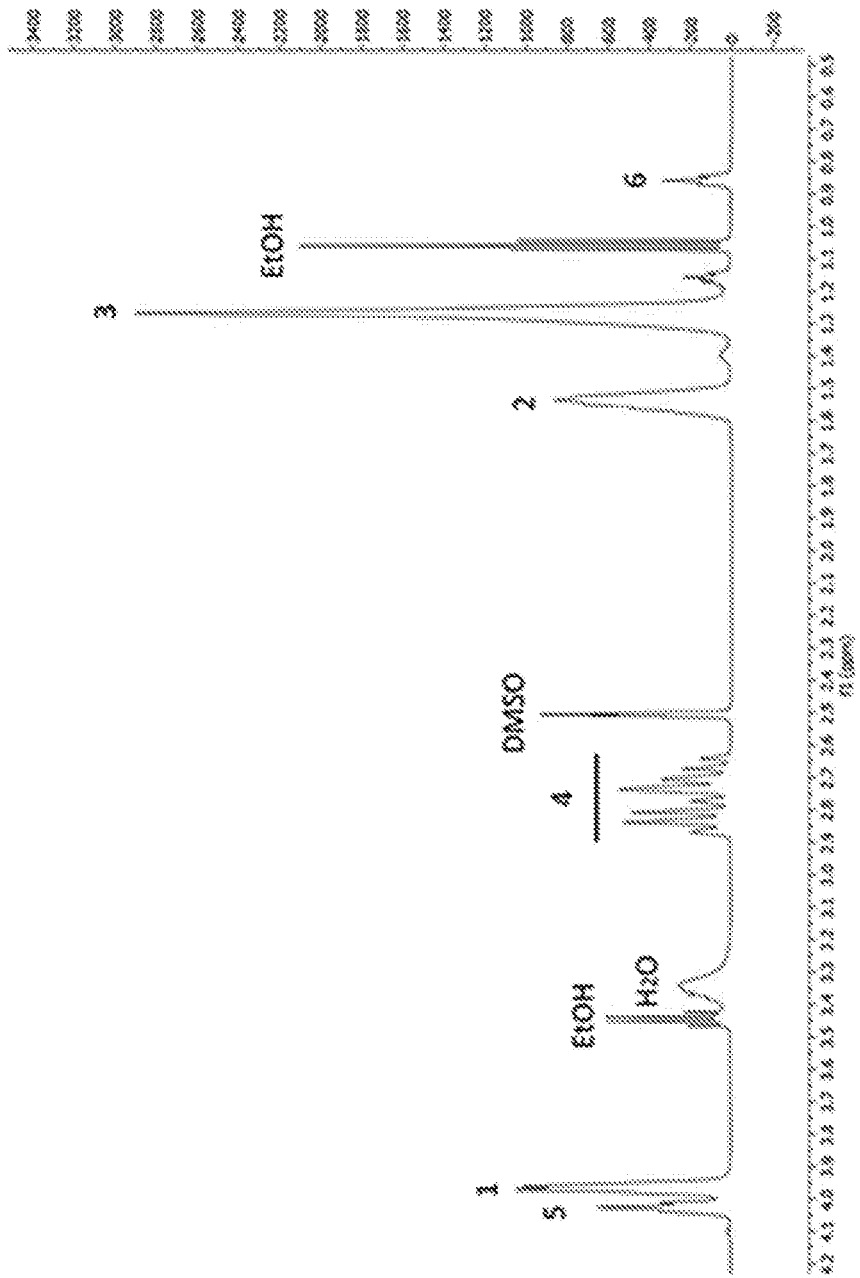
Figure 1D:
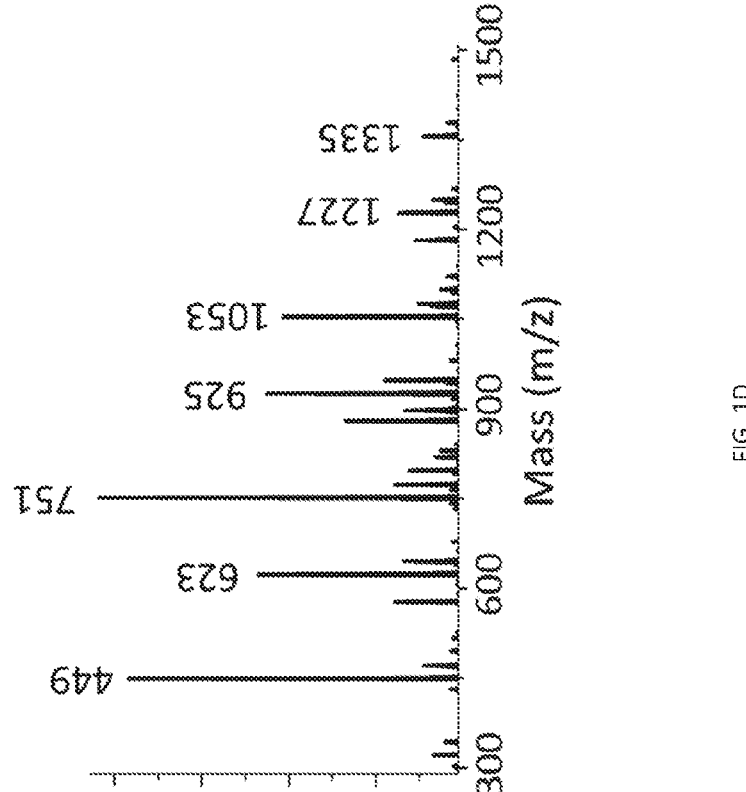
FIG. 1D-1E show the representative mass spectrum of POC (D) and POOC pre-polymer (E).
Figure 1E:
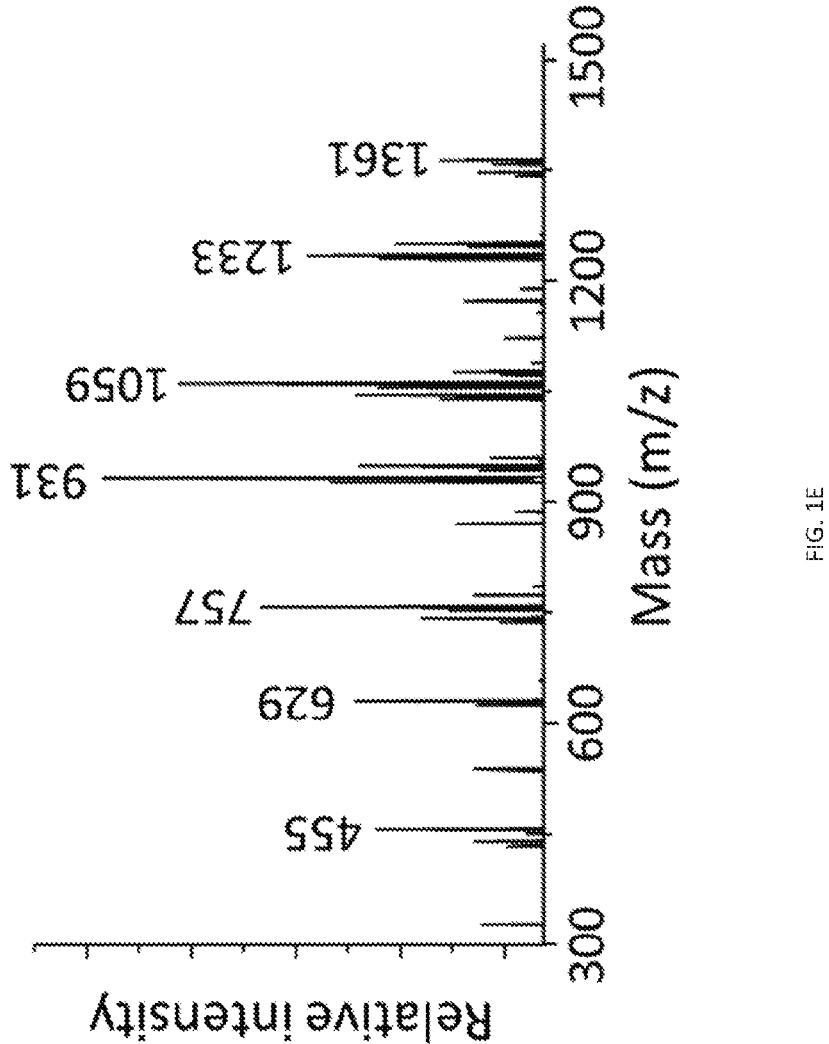

Synthesis and Purification of POOC Pre-Polymer:

The POOC pre-polymer was synthesized by the reactions of 1,8-octanediol, citric acid, and 1-octanol with various molar ratios of 1:1:0 (0%), 0.95:1:0.1 (10%), 0.9:1:0.2 (20%), and 0.85:1:0.3 (30%) (FIG. 1A). The three compo- nents were mixed in a round bottom flask and heated to 160° C. for melting in a silicon oil bath under a flow of nitrogen gas with stirring. The flask was then transferred into 140° C. oil bath and continued stirring for another 1-3 h under a flow of nitrogen gas. The flask was subsequently put into an ice bath to stop the reaction. For purification, ethanol was added into the flask to dissolve the pre-polymer under shaking. The solution was precipitated in 20% ethanol solution. The precipitation of the POOC pre-polymer was freeze-dried followed by dissolving in ethanol to prepare 40% POOC pre-polymer solution. NMR and mass spectrums were used to characterize the POC and POOC pre-polymer. According to the NMR spectrum, there is an obvious peak at 0.85 ppm that represents the methyl group (FIG. 1B-1C). Mass spec- trum also showed different mass to charge ratio (m/z) of POC and POOC pre-polymer (FIG. 1D-1E). The molecular compositions of each m/z peak are listed in Table 1 and Table 2. All these results showed that 1-octanol was conju- gated onto the pre-polymer as the capping reagent.

TABLE 1

| Molecular composition of POC pre-polymer according to mass spectrum. | | | |
|---|---|---|---|
| | Molecular number | | |
| Mass (m/z) | Citric acid | 1,8-octanediol | 1-octanol |
| 449 | 1 | 2 | 0 |
| 623 | 2 | 2 | 0 |
| 751 | 2 | 3 | 0 |
| 925 | 3 | 3 | 0 |
| 1053 | 3 | 4 | 0 |
| 1227 | 4 | 4 | 0 |
| 1355 | 4 | 5 | 0 |

TABLE 2

| Molecular composition of POOC pre- polymer according to mass spectrum | | | |
|---|---|---|---|
| | Molecular number | | |
| Mass (m/z) | Citric acid | 1,8-octandiol | 1-octanol |
| 455 | 1 | 1 | 1 |
| 629 | 2 | 1 | 1 |
| 757 | 2 | 2 | 1 |
| 931 | 3 | 2 | 1 |
| 1059 | 3 | 3 | 1 |
| 1233 | 4 | 3 | 1 |
| 1361 | 4 | 4 | 1 |

Casting and Leaching of POOC Scaffold 100 mL of 40% POOC solution was centrifuged to remove undissolved particles and transferred into a 17 cm×17 cm glass mold. The solution was left at room temperature overnight for solvent evaporation. Then the pre-polymer was post-polymerized at 70° C. for 5 days. The introduced octanol as the capping reagent can prevent growth of the polymer chain to reduce the crosslinking degree (dotted square in FIG. 1). After acquisition, the POOC scaffold was put into DMEM medium containing 20% ethanol to leach the unreacted monomer out. The medium was changed every 8 h for an initial 24 h. Then, the scaffold was further leached in DMEM medium for 3 d with medium changed twice a day. Finally, the scaffold was submerged in MSC complete medium for 7 days until cell seeding.

Figure 2A:
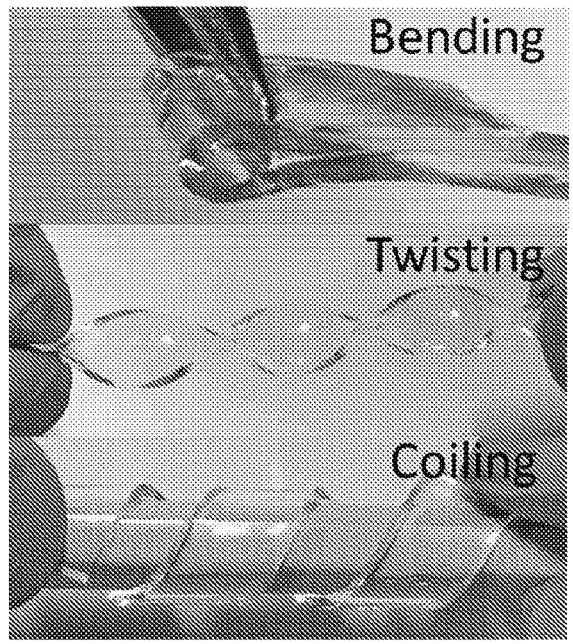
FIG. 2A-2C show the characterization of POC and POOC scaffolds.
Figure 2B:
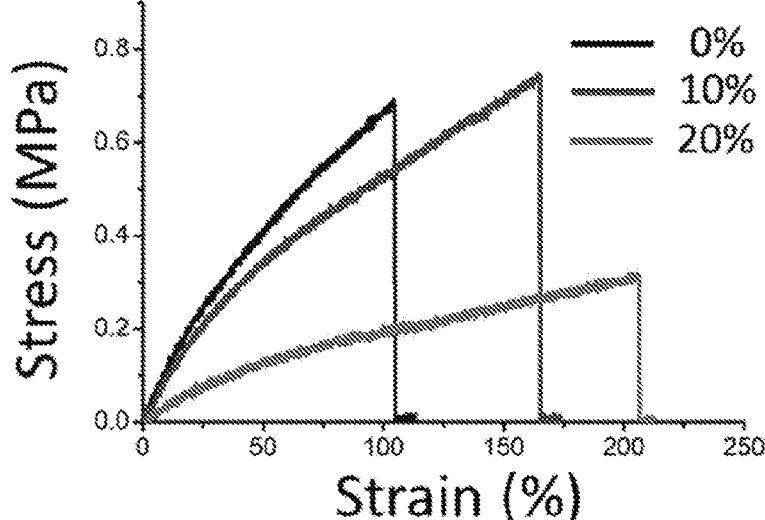
Figure 2C:
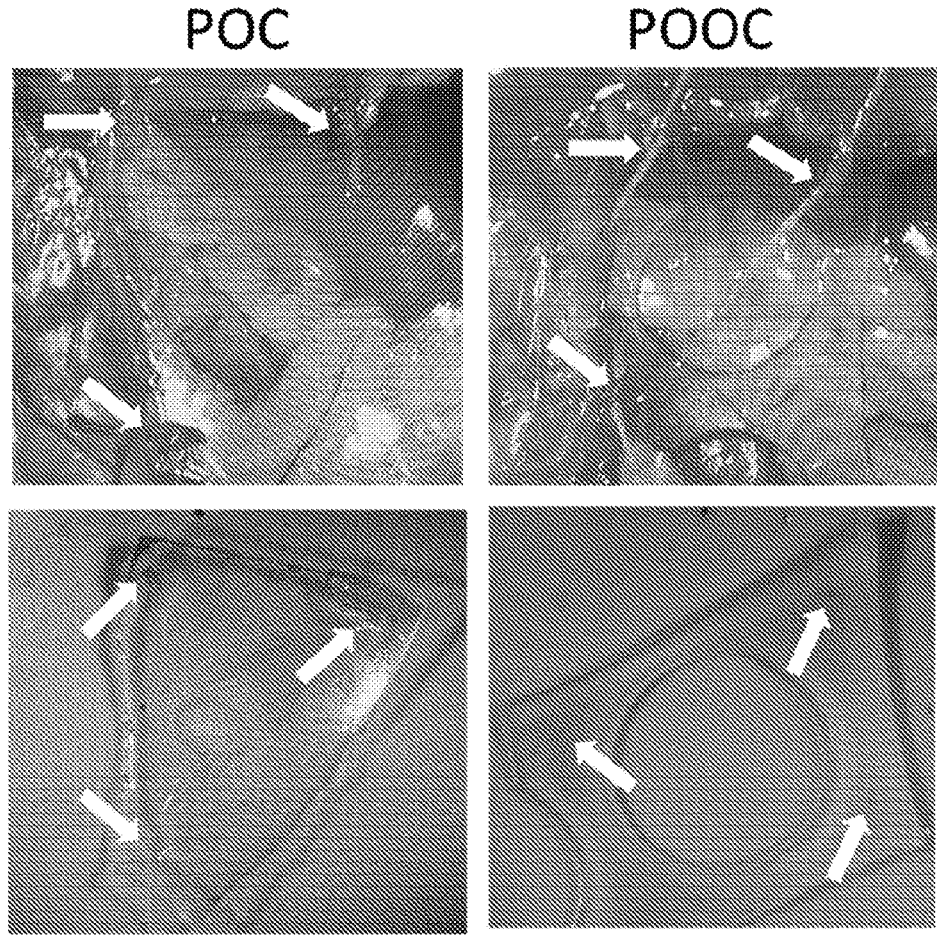

The hydrated POOC scaffold still had excellent deformability (FIG. 2A) and was more elastic than hydrated POC scaffold (FIG. 2B). The tensile moduls of the hydrated scaffolds decreased with the increase of 1-octanol content from 0% to 20%. However, the POOC scaffold with 30% of 1-octanol could not be fully cured under the same curing conditions which resulted in a non-elastic products. According to the reference (Dahms et al. Br J Urol 1998; 82(3): 411-419, incorporated herein by reference in it's entirety), a 20% POOC scaffold provided similar tensile modulus and tensile stress comparing to the mechanics of native tissue. Therefore, the 20% POOC scaffolds were used for further applications. The scaffolds were sutured onto the abdominal wall of mice followed by removal of sutures to check if any damage occurred to the scaffold during the surgery. Small cracks extended from the surture site can be observed in POC scaffold, but there was no obvious deformities in POOC scaffold (FIG. 2C)

Cell Seeding Process

Figure 3:
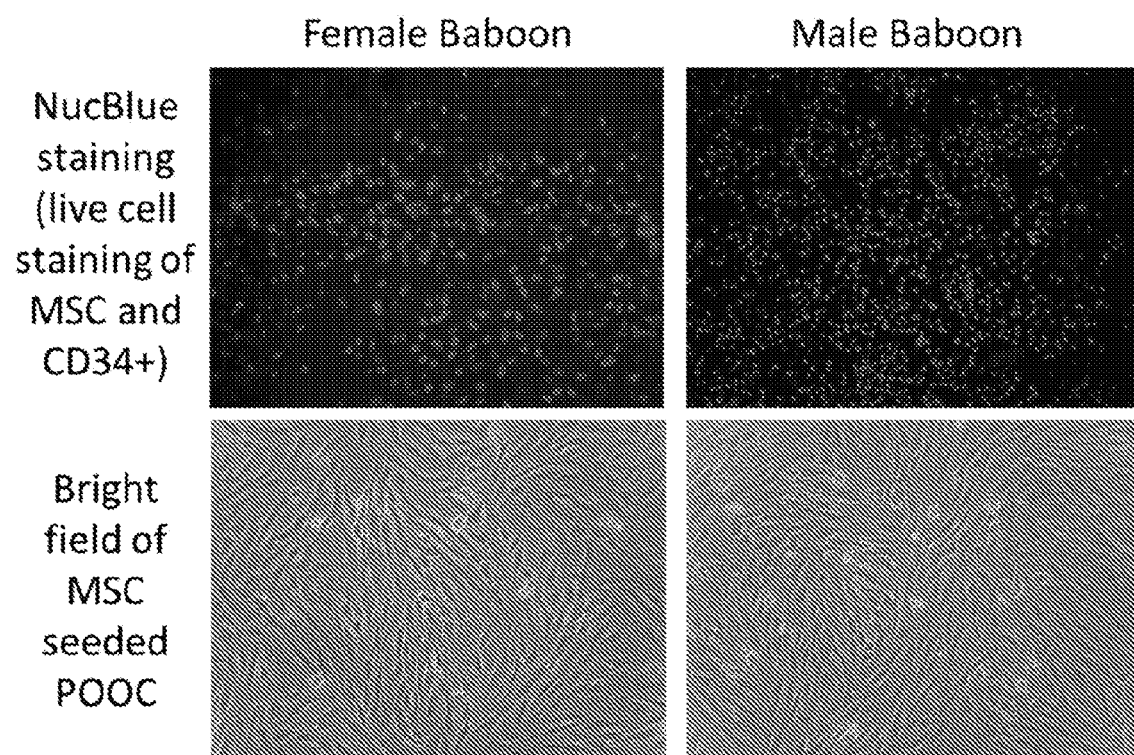
FIG. 3 shows images of cell-seeded POOC scaffold.

The cell seeding process was performed according to previous report (Sharma et al., *PNAS,* 110, 4003, 2013, incorporated herein by reference in it's entirety). MSCs and CD34$^+$ HSPCs collected from baboons were used for cell seeding. One week before surgery, MSCs were seeded onto POOC scaffold at a density of 30,000 cells/cm$^2$. After initial seeding, majority of the scaffold was covered by cells. Three days before surgery, additional MSC seeding (10,000 cells/cm$^2$) was performed to completely cover the scaffold. At one day prior to surgery, a combination of MSCs (15,000 cells/cm$^2$) and CD34$^+$ HSPCs (a variable number depending on bone marrow aspiration) were suspended in a mixture of MSC media and StemSpan SFFM media (1:1) and was seeded onto the scaffold. Based upon fluorescence staining of cell seeded scaffolds using NucBlue (life cell staining of MSC and CD34+ cells), the cells attached well and demonstrated a typical cellular morphology on POOC scaffolds (FIG. 3).

Example 2—Urinary Bladder Augmentation

Urinary bladder augmentation was performed in baboons (Papio anubis) with cell seeded POOC scaffolds in the following manner: the surgical area was initially shaved and prepared with repeated washes of isopropanol alcohol and betadine to sterilize the surgical area and limit the potential of subsequent infection. A transurethral catheter was then placed into the urinary bladder prior to surgery followed by the urinary bladder infusion with sterile saline and contrast reagent to positively identify the urinary bladder. Following a vertical midline incision, an approximate 50% supratrigonal cystectomy was performed on the urinary bladder. Mesenchymal stem cell (MSC) and CD34+ hematopoietic stem/progenitor cells (CD34+ HSPC) seeded POOC scaffold [6 cm (width)×7 cm (length)×1.5 mm (thickness); POOC scaffold seeded at a density of approximately 30,000 MSC cells/cm$^2$ and CD34+ HSPCs (a variable number depending on bone marrow aspiration) were used for augmentation. Cell/scaffold composites were then anastomosed to the urinary bladder with a single layer 5-0 polydioxanonesuture in a watertight manner. A suprapubic catheter was also inserted that exited the native urinary bladder for additional drainage in along with a penrose drain to relieve any extra leakage. The incision was closed in three layers: 2-0 polydioxanone suture was used to close the body wall, 3-0 polydioxanone suture was used to close the subcutaneous layer, and 3-0 polydioxanone suture was used to close the skin in a buried subcuticular pattern.

Figure 4:
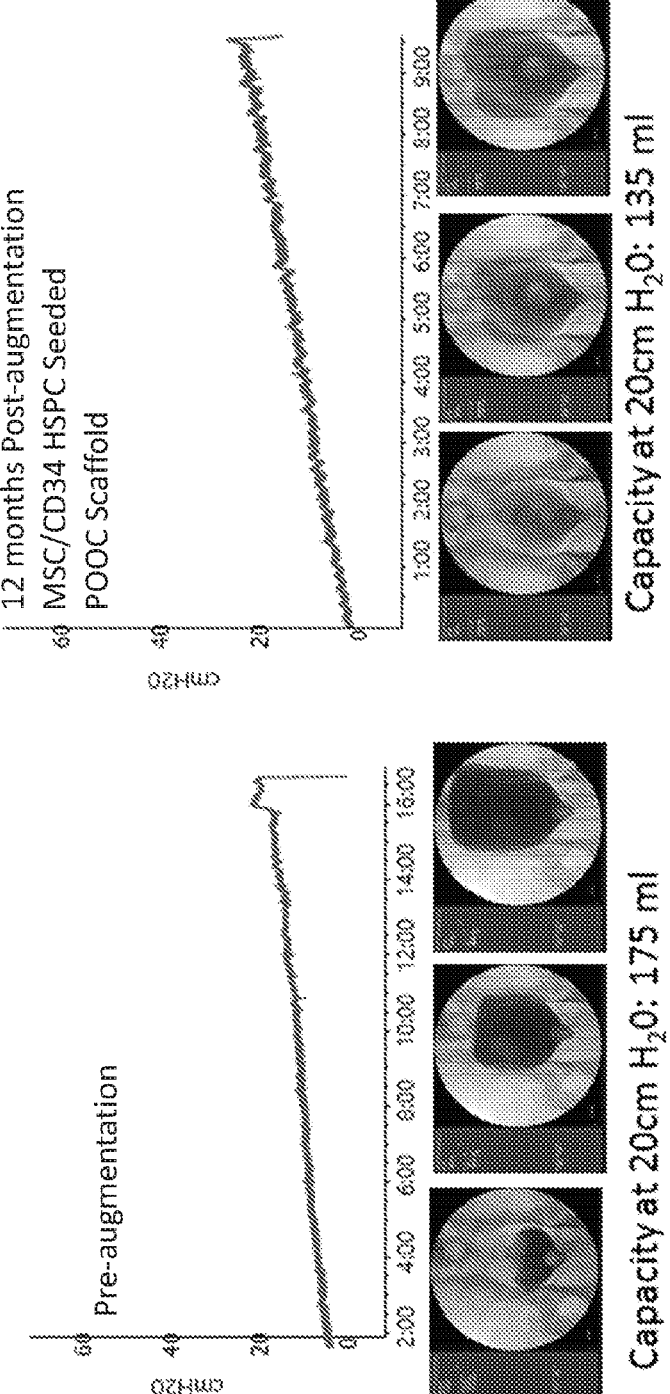
FIG. 4 shows exemplary data following urinary bladder augmentation in baboons (Papio anubis) with cell seeded POOC scaffolds. Urodynamics data demonstrate a return to normal compliance, filling and voiding pattern when comparing non-human primate pre-surgery values to MSC/CD34$^+$ HSPC seeded POOC scaffolds at the 12 month time-point. The urinary bladder capacity appears to be in a recovery phase.

The results from these procedures were able to show that the POOC material showed a greater ability to be sutured, and the material is more pliable when trying to conform to the shape of the native baboon urinary bladder when compared to the POC material. The POOC animals were also able to show a better urinary bladder capacity recovery. POOC Animal 1 pre-augmentation urinary bladder capacity was 166 milliliters (mls) and 6 months post-augmentation urinary bladder capacity was 160 mls, when compared to POC animal 1 pre-augmentation urinary bladder capacity was 200 mls and 6 months post-augmentation urinary bladder capacity was 60 mls. As shown in FIG. 4, POOC animal 2 pre-augmentation showed a capacity of 175 mls, and at 12 months post-augmentation capacity was 135 mls.

What is claimed is:

1. A cell transplantation system comprising:
   a. a poly (octamethylene-octanol citrate) (POOC) scaffold comprising 10-25% 1-octanol; and
   b. a population of cells.

2. The system of claim 1, wherein the population of cells comprises a population of mesenchymal stem cells (MSCs), a population of hematopoietic stem/progenitor cells (HSPCs), or a mixture of mesenchymal stem cells and HSPCs.

3. The system of claim 2, wherein greater than 50% of the cells in the population of HSPCs are CD34$^+$ HPSCs.

4. The system of claim 3, wherein greater than 90% of the cells in the population of HSPCs are CD34$^+$ HPSCs.

5. The system of claim 2, wherein the MSCs are bone marrow mesenchymal cells.

6. The system of claim 1, wherein the scaffold is seeded with the population of cells.

7. The system of claim 1, wherein the POOC scaffold comprises 10-20% 1-octanol.

8. The system of claim 7, wherein the POOC scaffold comprises 20% 1-octanol.

9. The cell transplantation system of claim 1 for use in a method of regenerating tissue in a subject in need thereof.

10. The cell transplantation system of claim 9, wherein the tissue is urinary bladder tissue.

11. The cell transplantation system of claim 9, wherein the subject is human.

* * * * *